United States Patent [19]

Matsuzawa et al.

[11] Patent Number: 4,670,650
[45] Date of Patent: Jun. 2, 1987

[54] METHOD OF MEASURING RESIST PATTERN

[75] Inventors: Toshiharu Matsuzawa, Shinzyuku; Kozo Mochiji, Hachioji, both of Japan

[73] Assignee: Hitachi, Ltd, Tokyo, Japan

[21] Appl. No.: 737,481

[22] Filed: May 24, 1985

[30] Foreign Application Priority Data

May 25, 1984 [JP] Japan .............................. 59-104529

[51] Int. Cl.[4] .................... G01N 23/227; H01L 21/00
[52] U.S. Cl. ................................. 250/307; 250/491.1
[58] Field of Search ............ 250/306, 307, 310, 491.1, 250/492.1, 492.2, 492.3; 324/71.3, 71.5

[56] References Cited

U.S. PATENT DOCUMENTS 3,703,637 11/1972 Dugan ................................. 250/307
4,495,262 1/1985 Matsuzaki et al. .................... 357/37

FOREIGN PATENT DOCUMENTS 0031527 2/1983 Japan ............................... 250/492.2

OTHER PUBLICATIONS

Pocker et al., High Spatial Resolution Auger Spectroscopy and Auger Integration Applications, J. Vac. Sci. Technol., vol. 12, No. 1, Jan./Feb. 1975.
Todd et al., Auger Electron Spectroscopy at High Spatial Resolution and nA Primary Beam Currents, J. Vac. Sci. Technol., vol. 12, No. 4, Jul./Aug. 1975.
Kaplan et al, "Repair of Mask-Caused Defects in a Positive Working Photoresist Pattern", IBM Tech. Dis. Bul., vol. 8, No. 6, Nov. 65.

Primary Examiner—Bruce C. Anderson
Assistant Examiner—Paul A. Guss
Attorney, Agent, or Firm—Antonelli, Terry & Wands

[57] ABSTRACT

A method of measuring a resist pattern in which size and/or position of a latent image formed in the resist film by irradiation, is measured by Auger electron spectroscopy or a like method. With this method, since there is no need to develop when the resist pattern is not acceptable, manufacturing costs are decreased. By adjusting developing time by replying upon the data from the latent image, furthermore, high yield processing can be effected more precisely.

11 Claims, 3 Drawing Figures 4,670,650

METHOD OF MEASURING RESIST PATTERN

BACKGROUND OF THE INVENTION

The present invention relates to a method of measuring resist patterns used in microlithography, particularly to a method of measuring resist patterns that is adapted to reducing manufacturing costs microlithography for manufacturing integrated circuits and that is adapted to automatically controlling the manufacturing steps, and further relates to a method of measuring the width and alignment of the resist pattern.

So far, it is accepted practice to measure resist patterns, i.e., to measure the pattern width of resists or to measure mask alignment error with respect to a different layer, after the developing has been conducted. When a measured value falls out of a specified value, it is necessary to remove the resist pattern and to effect again the step of applying the resist, resulting in wasteful processing of developing. Namely, the developing time and the developing liquid are wasted, thereby increasing the manufacturing cost.

The inventors could not find any references related to the measurement of resist pattern.

SUMMARY OF THE INVENTION

The object of the present invention is to provide a technique for measuring the size of resist patterns or of mask alignment errors prior to developing the resist film. More specifically, the present invention provides a method of measuring resist pattern by detecting a latent image formed in the resist.

In order to achieve the above-mentioned object, a latent image, formed in the resist film by the irradiation of rays, is measured by spectroscopy or electron spectroscopy in the method of measuring resist pattern of the present invention.

A resist reacts with the irradiation such as light, electron beam, X-ray, ion beam or the like, and undergoes chemical changes such as changes in chemical composition. The portions that have undergone the change form a latent image. If the change is detected by spectroscopy or electron spectroscopy, for example, as a change in the distribution of elements, it is possible to detect the size and position of the latent image.

The quality of the resist pattern is evaluated by the size and/or the position of the thus detected latent image. When the quality is acceptable, the resist pattern is subjected to developing. When the quality is not acceptable, the resist pattern is removed, and the step of applying the resist is carried out again. This helps eliminate waste in the developing operation.

Further, it is good practice to clarify in advance the relation between the size of the latent image obtained as mentioned above and developing conditions which help obtain the optimum size—for example, to prepare a graph showing the relations between the size of the latent image, size of image after development, and developing time—and to develop relying upon such a relation under developing conditions corresponding to the size of the latent image. Then, the resist film that would not have been acceptable up to now can be turned into a resist pattern that is acceptable.

Relying upon the data of size of the obtained latent image, furthermore, the amount of energy irradiated on the resist film or the pre-baking temperature of the resist film is adjusted, in order to more precisely define the size of the resist pattern that is formed subsequently.

A particularly preferred method of spectroscopy may be Auger electron spectroscopy. However, any method of spectroscopy or electron spectroscopy, which detects the distribution of chemical changes such as the distribution of elements, may be utilized. For example, spectroscopy which is based upon the measurement of the refractive index of light can be shown.

Further, the latent image of the resist film can be detected by examining the distribution of elements on the surface of the resist film. No limitation is imposed on the thickness of the resist film to detect the size of latent image of the resist pattern; i.e., the resist film may be formed so as to have a thickness required for the microlithography. However, when a target mark formed under the resist is to be measured by an electron beam in order to measure the misalignment of latent image, the pattern will have to be detected by relying upon an image reflected by a primary electron beam. Therefore, the resist film must be thin enough to permit the transmission of primary electron beam. Usually, a resist film that is 1 $\mu$m thick permits a primary electron beam to pass through. By increasing the acceleration voltage, however, the electron beam can pass through the resist film having an increased thickness.

DESCRIPTION OF THE PREFERRED EMBODIMENTS

EXAMPLE 1

A positive working photoresist was applied onto a silicon wafer substrate, prebaked at a temperature of 90° C., and, according to the well-known method, was irradiated with ultraviolet light through a photomask having a predetermined pattern to form unirradiated portions and irradiated portions. AZ 1350 J (trade name, Shipley Co., U.S.A.) was used as the positive working photoresist. The resist was 1 $\mu$m thick, and the size of the irradiated portion was 1 $\mu$m in width and 2 $\mu$m in length.

Figure 1:
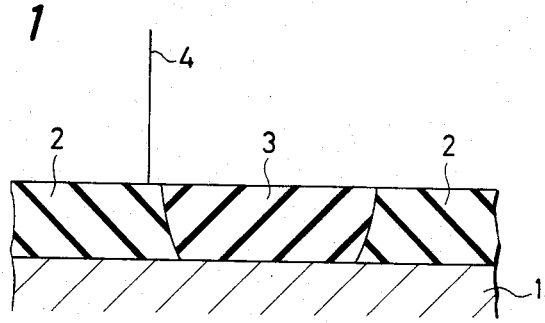
FIG. 1 is a section view showing a latent image of resist on a flat silicon wafer in an embodiment of the present invention.

FIG. 1 is a section view of a latent image of a resist formed as mentioned above, wherein reference numeral 1 denotes the silicon wafer substrate, 2 denotes the unirradiated portion of the photoresist, 3 denotes the irradiated portion of the photoresist, and 4 denotes a detecting electron beam.

After ultraviolet irradiation, the silicon wafer substrate was scanned with a detecting electron beam 4 using the well known Auger electron spectrometer to measure the distribution of nitrogen, in order to discriminate the ultraviolet irradiated portion 3 from the unirradiated portion 2, and to measure the pattern width of the latent image (irradiated portion 3 in this embodiment) of the aimed pattern. When the amount of nitrogen in the unirradiated portion 2 was assumed to be 100, the amount of nitrogen in the irradiated portion 3 was about 30.

Figure 2:
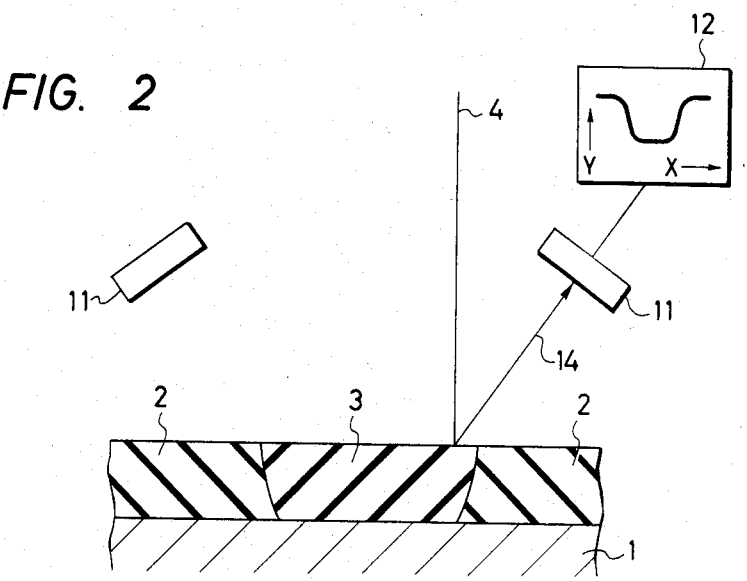
FIG. 2 is a schematic diagram which explains the principle for measuring the latent image of a resist in the exbodiment of the present invention.

FIG. 2 is a schematic diagram which explains the principle for measuring the latent image of resist. As the detecting electron beam 4 is allowed to be incident upon the resist surface, Auger electrons are generated and move in a direction designated at 14 and enter into a detector 11. Output signals of the detector 11 are input to a display 12 to measure the latent image. The X-axis of the display 12 represents the position of the detecting electron beam 4 with respect to the scanning direction and the Y-direction represents the amount of the aimed element. Other reference numerals of FIG. 2 represent the same portions as those of FIG. 1.

According to this embodiment, a resist pattern having error of greater than ±0.3 μm relative to the pattern width of 1 μm was regarded as unacceptable. Then, the unacceptable ratio of the resist pattern was about 20%. The unacceptable resist was removed from these wafers instead of developing them, and resist was applied to them again, thus avoiding an unnecessary developing operation. According to this embodiment, furthermore, correction data were prepared beforehand to clarify the relation between the size of the latent image, size of pattern after developing and the developing conditions. Using the calibration data, the width of resist pattern that had deviated by more than ±0.15 μm from the aimed value could be detected after developing by relying upon the measured data of the latent image.

In this embodiment, the distribution of nitrogen was measured by Auger electron spectroscopy by utilizing the fact that a compound (quinonediazide) containing nitrogen, that constitutes a photoresist sensitizer, releases nitrogen upon irradiation with ultraviolet light, and the concentration of nitrogen decreases in the irradiated portions.

EXAMPLE 2

Figure 3:
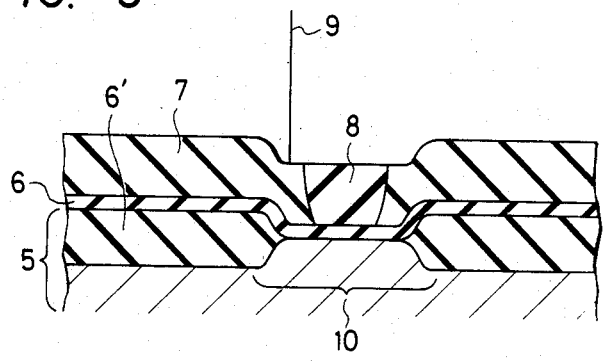
FIG. 3 is a section view showing the latent image of resist on a silicon wafer having a step employed in a target pattern according to another embodiment of the present invention.

In order to process a thin SiO₂ film 6 on a silicon wafer substrate 5 having a step 10 employed in a target pattern 10 as shown in FIG. 3, an electron beam resist consisting chiefly of a phenolic resin and polymethylpentenesulfon was applied, prebaked at a temperature of 100° C., and circuit patterns were delineated thereon by irradiation of a writing electron beam in a well-known manner using an electron beam writing machine, to form an unirradiated portion 7 and an irradiated portion 8. Following the electron beam writing, both the unirradiated portion and the irradiated portion of the resist were scanned with a detecting electron beam 9 using the Auger electron spectrometer installed in the electron beam writing machine, and the distribution of sulfur was measured, in order to discriminate the portion 8 irradiated with the writing electron beam over the portion 7 not irradiated with the electron beam and to measure the pattern width of an aimed latent image (irradiated portion 8 in this embodiment). RE 5000 P (a trade name of Hitachi Chemical Co., Ltd. of Japan) was used as the electron beam resist. The resist was 0.6 μm thick, and the size of the irradiated portion was 0.8 μm in width and 2 μm in length. In this embodiment, there was used the Auger electron spectrometer installed in the electron beam writing machine. However, it is also allowable to use an external Auger electron spectrometer. In FIG. 3, furthermore, reference numeral 6' denotes a silicon oxide film formed by the thermal oxidation.

In this embodiment, when the amount of sulfur in the unirradiated portion 7 was assumed to be 100, the amount of sulfur in the portion 8 irradiated with the electron beam was about 10.

The principle for measuring the latent image of resist was the same as that of Example 1.

In this embodiment, a resist pattern having a error greater than ±0.25 μm relative to the pattern width of 0.8 μm was regarded as unacceptable. Then, the unacceptable ratio of the resist pattern was about 10%, and unnecessary developing of the substrate was avoided at a corresponding ratio. By using the calibration data that had been prepared in advance in the same manner as in Example 1, furthermore, the width deviation of resist pattern after developing, by more than ±0.15 μm from the aimed value, could be detected relying upon the measured data of latent image.

In this embodiment, the distribution of sulfur was measured by Auger electron spectroscopy. Since sulfur contained in the polymethylpentenesulfon was released upon irradiation with the electron beam, the irradiated portion could be detected simply by measuring the distribution of sulfur.

In the case of this embodiment, not only the pattern width of the latent image could be measured, but also misalignment of the latent image could be measured maintaining a precision of ±0.05 μm by detecting the target pattern 10 formed under the resist by the reflected image of the primary electron beam in the conventional manner and by comparing the data from the target mark with the data from the position of the latent image.

According to the present invention as described above, the size and/or the position of the latent image can be detected prior to developing the resist. When the size and/or position fall outside the specified values, therefore, unnecessary development is not performed; development is effected only when size and position lie within the specified values, thereby enabling the process to be carried out efficiently and the manufacturing cost to be reduced. Furthermore, if developing time is adjusted by relying upon the data from the resist pattern obtained by the invention, it is possible to limit the size of the pattern after development within a specified range even when the size of latent image falls outside the specified range. That is, if the developing time is extended, in general, the increased portion of the resist dissolves. Therefore, when it is desired to correctly define the width of the irradiated portion with a positive working resist, developing time should be extended if the latent image is too small, and shortened if the latent image is too large. Further, if the relation between the pattern width of latent image, developing time and pattern width after developing, is known in advance, developing time can be adjusted very easily.

Moreover, if the relation between the amount of irradiation, prebaking temperature, pattern width of latent image, and pattern width after developing, is known in advance, the pattern can be formed very precisely by controlling the irradiation or the prebaking temperature employing the obtained data of the latent image.

Using the method of measuring resist pattern of the present invention, therefore, control conditions can be learned quickly so as to form the pattern precisely; therefore this method of measuring the resist pattern of the present invention is ideally suited for automatic control.

Although a positive working resist was used in the above embodiment, it needs not be pointed out that a negative working resist could also be used.

In the method of measuring the resist pattern of the present invention, furthermore, reference should be made to microlithography, spectroscopy, electron spectroscopy and the like that have heretofore been known in the field of the present invention, concerning those that have not been described in the specification of the present application.

Obviously many modifications and variations of the present invention are possible in the light of the above explanation. It is therefore to be understood that within the scope of the appended claims the invention may be practiced otherwise than as specifically described.

What is claimed is:

1. A method of measuring a resist pattern wherein a pattern width and/or misalignment of a latent image formed in a resist film on a substrate by irradiation, is measured by determining the distribution of elements within said resist film and said latent image relying upon Auger electron spectroscopy.

2. A method of measuring a resist pattern according to claim 1, wherein said substrate has a target mark, and an image of said target mark obtained by the reflection of primary electron beam incident upon the substrate is compared with the measurement of said latent image obtained by the method of said Auger electron spectroscopy, to measure alignment error of said latent image.

3. A method of measuring a resist pattern according to claim 1, wherein said resist is a photoresist.

4. A method of measuring a resist pattern according to claim 3, wherein said photoresist contains quinonediazide as a sensitizer, and said latent image is measured by determining the distribution of nitrogen.

5. A method of measuring a resist pattern according to claim 1, wherein said resist is an electron beam resist.

6. A method of measuring a resist pattern according to claim 5, wherein said electron beam resist contains polymethlpentenesulfon, and said latent image is determining by measuring the distribution of sulfur.

7. A method of measuring a resist pattern according to claim 1, wherein the pattern width of said latent image is measured.

8. A method of measuring a resist pattern according to claim 1, wherein misalignment of said latent image is measured.

9. A method of measuring a resist pattern according to claim 1, wherein the pattern width of said latent image and misalignment are measured.

10. A method of measuring a resist pattern according to claim 8, wherein said resist film is formed on a substrate that has a target mark for mask-alignment.

11. A method of measuring a resist pattern according to claim 9, wherein said resist film is formed on a substrate that has a target pattern.

* * * * *